US009605302B2

(12) United States Patent
O'Halloran (10) Patent No.: US 9,605,302 B2
(45) Date of Patent: Mar. 28, 2017

(54) SENSING STRATEGIES AND METHODS FOR NUCLEIC ACID DETECTION USING BIOSENSORS (75) Inventor: Jonathan O'Halloran, Uckfield (GB)

(73) Assignee: QuantuMDx Group Limited, Newcastle upon Tyne (GB)

( * ) Notice: Subject to any disclaimer, the term of this patent is extended or adjusted under 35 U.S.C. 154(b) by 0 days.

(21) Appl. No.: 13/062,213

(22) PCT Filed: Sep. 3, 2009

(86) PCT No.: PCT/IB2009/005008
§ 371 (c)(1),
(2), (4) Date: Mar. 3, 2011

(87) PCT Pub. No.: WO2010/026450
PCT Pub. Date: Mar. 11, 2010

(65) Prior Publication Data
US 2011/0294685 A1 Dec. 1, 2011

Related U.S. Application Data (60) Provisional application No. 61/094,017, filed on Sep. 3, 2008.

(51) Int. Cl.
C12Q 1/68 (2006.01)

(52) U.S. Cl.
CPC ......... *C12Q 1/6825* (2013.01); *C12Q 1/6848* (2013.01)

(58) Field of Classification Search
None
See application file for complete search history.

(56) References Cited

U.S. PATENT DOCUMENTS

| 5,350,687 | A | * | 9/1994 | Odink | C07K 14/52 |
| | | | | | 435/335 |
| 5,677,125 | A | * | 10/1997 | Holt | C07K 14/82 |
| | | | | | 435/6.14 |
| 6,656,692 | B2 | * | 12/2003 | Erikson | C12Q 1/6816 |
| | | | | | 435/6.12 |
| 8,404,658 | B2 | * | 3/2013 | Hajjar | C12N 15/113 |
| | | | | | 514/44 |
| 2003/0186238 | A1 | * | 10/2003 | Allawi | C12N 9/1252 |
| | | | | | 435/6.18 |
| 2004/0010815 | A1 | * | 1/2004 | Lange | C07K 14/415 |
| | | | | | 800/278 |
| 2005/0123958 | A1 | | 6/2005 | Tsuchiya | |
| 2005/0164205 | A1 | | 7/2005 | Puskas | |
| 2008/0003693 | A1 | * | 1/2008 | Torres | G01N 33/68 |
| | | | | | 436/501 |
| 2008/0076121 | A1 | * | 3/2008 | Wolber | 435/6 |

FOREIGN PATENT DOCUMENTS

| WO | WO 97/28282 A1 | 8/1997 |
| WO | WO 02/063030 A2 | 8/2002 |
| WO | WO 03/052139 A1 | 6/2003 |
| WO | WO 03/091406 A2 | 11/2003 |
| WO | WO 03/100096 A1 | 12/2003 |
| WO | WO 2006/095981 A1 | 9/2006 |
| WO | WO 2006/097320 A2 | 9/2006 |
| WO | WO 2006/105360 A1 | 10/2006 |
| WO | WO 2007/077952 A1 | 7/2007 |
| WO | WO 2009/006445 A2 | 1/2009 |

OTHER PUBLICATIONS

Yao et al. Journal of Biological Chemistry (1994) 269(23): 16260-16268.*
Tanaka et al. Journal of the American Chemical Society (May 2007) 129: 5612-5620.*
Blais, B.W. Applied and Environmental Microbiology (1994) 60(1): 348-352.*
Yoo et al. Journal of Biological Chemistry 255: 10559-10562 (1980).*
Costa et al., Characterization in vitro and in vivo of the putative multigene 4-coumarate: CoA ligase network in Arabidopsis: syringyl lignin and sinapate/sinapyl alcohol derivative formation, Phytochemistry, Sep. 1, 2005, vol. 66, No. 17, pp. 2072-2091.
International Search Report dated Mar. 3, 2010, for International Application No. PCT/IB2009/006976.
International Search Report dated Feb. 19, 2010, for International Application No. PCT/IB2009/005008.
International Search Report dated Feb. 17, 2010, for International Application No. PCT/IB2009/007025.
Maki, W.C. et al., Universal bio-molecular signal transduction-based nano-electronic bio-detection system, Sensors and Actuators B, Aug. 12, 2008, vol. 133, No. 2, pp. 547-554.
Star, A. et al., Label-free detection of DNA hybridization using carbon nanotube network field-effect transistors, Proceedings of the National Academy of Sciences of USA, Jan. 24, 2006, vol. 103, No. 4, pp. 921-926.
Wu, F. Y.-H. et al., Synthesis and properties of adenosine-5'-triphosphoro-gamma-1-(5-sulfonic acid)naphthyl ethylamidate: A fluorescent nucleotide substrate for DNA-dependent RNA polymerase from *Escherichia coli*, Archives of Biochemistry and Biophysics, May 1, 1986, vol. 246, No. 2, pp. 564-571.
Zhu, Z. et al., Molecular mechanism controlling the incorporation of fluorescent nucleotides into DNA by PCR, Cytometry, Jan. 1, 1997, vol. 28, pp. 206-211.

* cited by examiner

Primary Examiner — Angela M Bertagna
(74) Attorney, Agent, or Firm — Knobbe Martens Olson & Bear LLP (57) ABSTRACT Embodiments of the present invention relate generally to strategies and methods of amplifying short target sequences and removing flanking sequences from target nucleic acids to remove background signal when detecting hybridizations events using sensitive detection biosensors, such as biosensors based on nanowires, carbon nanotubes, nanopores etc, that may be capable of detecting molecules at small molar concentrations (fM and less), or even at the single molecule level. Furthermore, by cropping and therefore standardizing the size of the target sequences to be detected, when detecting many target sequences in an array, the signals across each biosensor can be compared and the hybridization conditions standardized easily.

20 Claims, 3 Drawing Sheets

SENSING STRATEGIES AND METHODS FOR NUCLEIC ACID DETECTION USING BIOSENSORS

CROSS REFERENCE TO RELATED APPLICATIONS

This application is the national phase under 35 U.S.C. §371 of prior PCT International Application No. PCT/IB2009/005008 which has an International filing date of Sep. 3, 2009, designating the United States of America, which claims the benefit of U.S. Provisional Patent Application No. 61/094,017 filed on Sep. 3, 2008, the disclosures of which are hereby expressly incorporated by reference in their entirety and are hereby expressly made a portion of this application.

BACKGROUND OF THE INVENTION

Field of the Invention

Embodiments of the present invention relate generally to strategies and methods for detecting an analyte comprising nucleotide sequences.

Description of the Related Art

Detection and quantification of biomolecules in biological/clinical samples can in general be important for identification and quantification of biological molecular species that may be associated with diseases, for an accurate prognosis, prediction and/or diagnosis since the choice of treatment or prevention that is applied, and the outcome for the patient depends, in part, upon it. The choice of diagnostic protocol is important in a diagnosis since errors may lead to misdiagnosis and the incorrect treatment/prevention strategy being employed. Furthermore a lack of empirical evidence to support traditional symptom-based diagnoses can limit the efficacy of the diagnosis in some diseases.

SUMMARY OF THE INVENTION

A method of detecting an analyte comprising a target nucleotide sequence is disclosed in accordance with embodiments of the present invention. The method may comprise amplifying the target nucleotide sequence and optionally at least one additional nucleotide sequence with one or more primers comprising a 5' anchor region, a 3' extension region, and a bubble region therebetween, wherein at least part of the 5' anchor region is removed after amplification, thereby generating a probe; contacting the analyte with the probe under hybridizing conditions; detecting a signal related to the presence, level and/or sequence variation of the target nucleotide sequence. In some embodiments, the analytes may comprise DNA, RNA, or any derivatives thereof and/or the one or more primers may comprise nucleotide sequences that are cleaved by a nuclease, wherein the nuclease may be a restriction enzyme of DNA, and/or RNA. In some other embodiments, the nucleotide sequences cleaved by the nuclease may be present in at least one of the bubble region and the 5' anchor region and in some of such embodiments, the nucleotide sequences cleaved by the nuclease are not present in either the 3' anchor region or the target nucleotide sequence. In addition, in some other embodiments, the probe comprise DNA, RNA, or any derivatives thereof and often can be immobilized on a conducting medium. The conducting medium can be selected from the group consisting of a nanowire, a nanotube, a nanogap, a nanopore, a nanobead, and any other nanostructure capable of conducting an electrical current.

In some aspects of the present invention, the signal detected by the foregoing method can be generated when hybridization of the analyte to the probe causes a change in the electrical charge of the probe. The foregoing method can detect sequence variations in the target nucleotide sequence, and can further detect two or more of the presence, level and sequence variation of the target nucleotide sequence simultaneously. In some embodiments, the foregoing method may further comprise two or more types of probes, each of which comprises different nucleotide sequences.

An oligonucleotide primer for amplifying a target nucleotide sequence is also disclosed in accordance with embodiments of the present invention. The oligonucleotide may comprise a 5' anchor region, wherein the 5' anchor region is configured to hybridize to a nucleotide sequence outside of the target nucleotide sequence and is at least partially complimentary to the nucleotide sequence outside of the target nucleotide sequence; a 3' extension region, wherein the 3' extension region is configured to hybridize to a portion of the target nucleotide sequence; and a bubble region located between the 5' anchor region and the 3' extension region, wherein at least one of the 5' anchor region and the bubble region comprise a nuclease cleavage sequence. In one example, the oligonucleotide primer comprises the 5' anchor region is about 15 to 30 by and about 70 to 100% complimentary to the nucleotide sequence outside of the target nucleotide sequence; the 3' extension region is about 5 to 30 by and about 80 to 100% complimentary to the portion of the target nucleotide sequence, and wherein a melting temperature of the 3' extension region hybridized to the portion of the target nucleotide sequence is optimized such that the 3' extension region can only hybridize to the portion of the target nucleotide sequence under selective conditions when the 5' anchor region is hybridized to the nucleotide sequence outside of the target nucleotide sequence; and the bubble region is about 50% or less complimentary to the target nucleotide sequence, and comprises a nuclease cleavage sequence.

In preferred embodiments, the disclosed oligonucleotide primers facilitate PCR multiplexing in a single reaction and consistent amplification of short amplicons.

A biosensor for detecting an analyte in a sample, wherein the analyte comprises a target nucleotide sequence, is also disclosed in accordance with embodiments of the present invention. The biosensor in some embodiments may comprise a signal sensing unit, the signal sensing unit comprising a probe immobilized on a conducting medium, wherein the probe is prepared by amplifying the target nucleotide sequence and optionally at least one additional nucleotide sequence with one or more primers comprising a 5' anchor region, a 3' extension region, and a bubble region therebetween, wherein at least part of the 5' anchor region is removed after amplification; a signal detecting unit operably coupled to the conducting medium of the signal sensing unit; and a signal processing unit operably coupled to the signal detecting unit. The foregoing biosensor in some examples may comprise the signal processing unit, which further comprises one of more of a signal sensing unit, a signal recording unit, a data processing unit, and a data reporting unit.

According to one aspect of the present invention, the foregoing method of detecting an analyte, which comprises a target nucleotide sequence, may comprise obtaining the analyte; contacting the analyte with a probe, which is immobilized on a conducting medium, under hybridizing conditions, wherein the probe is at least partially complimentary to the target nucleotide sequence, such that the probe hybridizes to the target nucleotide sequence, thereby generating a duplex of the target nucleotide sequence and the probe; removing single stranded nucleotide sequences that are not present in the duplex; and detecting a signal related to the presence, level and/or sequence variation of the target sequence.

According to another aspect of the present invention, the foregoing method of detecting an analyte, which comprises a target nucleotide sequence, may comprise obtaining the analyte comprising the target nucleotide sequence; contacting the analyte with an oligonucleotide, wherein the oligonucleotide hybridizes to the target nucleotide sequence, thereby generating a duplex of the target nucleotide sequence and the oligonucleotide; removing single stranded nucleotide sequences that are not present in the duplex; obtaining the target nucleotide sequence from the duplex; contacting the obtained target nucleotide sequence with a probe, which is immobilized on a conducting medium, under hybridizing conditions, wherein the probe is at least partially complimentary to the target nucleotide sequence, such that the probe hybridizes to the target nucleotide sequence, thereby generating a duplex of the target nucleotide sequence and the probe; and detecting a signal related to the presence, level and/or sequence variation of the target nucleotide sequence.

In some embodiments, the probe used in any of the foregoing methods detecting an analyte can be generated by amplifying the target nucleotide sequence and optionally at least one additional nucleotide sequence with one or more primers comprising a 5' anchor region, a 3' extension region, and a bubble region therebetween, wherein at least part of the 5' anchor region is removed after amplification. In some other embodiments, at least one of the 5' anchor region and the bubble region of the probe may comprise a nuclease cleavage sequence. In addition, the analyte detected in any of the foregoing methods can be obtained by one of the following methods: amplifying the analyte comprising the target nucleotide sequence with one or more primers comprising nucleotide sequences corresponding to part of the target nucleotide sequence, obtaining nucleotide sequences from an organism and sheering the nucleotide sequences into a size suitable for contacting with the probe, and obtaining nucleotide sequences from an organism and cleaving the nucleotide sequences using one or more nucleases into a size suitable for contacting with the probe.

For some of the foregoing methods of detecting an analyte, which may remove single stranded nucleotide sequences, such cleavage of the single stranded nucleotide sequences may use one or more nucleases. In some cases, the one or more nucleases comprise sequence-specific nucleases and/or sequence-nonspecific nucleases. In some other cases, the one or more nucleases may be selected from S1 nuclease, P1 nuclease, micrococcal nuclease, mung bean nuclease, exonuclease, II, III, IV, V, VI, VII and VIII, and Klenow fragment.

DETAILED DESCRIPTION OF THE PREFERRED EMBODIMENT

There are some methods and protocols for detecting and quantifying biological molecules and compounds. These include, Enzyme Linked Immunosorbant Assay (ELISA), microarrays, electrophoresis, cell culture etc. Each method may be suited to a particular biological molecular species and exhibit a variety of different sensitivities. Sensitive detection biosensors, such as biosensors based on nanowires, carbon nanotubes, nanopores, nanobeads, and nanogaps, etc, often require new molecular biological strategies to facilitate detection due to their sensitive detection methods that may be capable of detecting molecules at small molar concentrations (fM and less), or even at the single molecule level (See e.g., U.S. Pat. Nos. 7,129,554, 7,256,466, 7,385,267, and U.S. patent application Ser. No. 12/038,794, which are incorporated herein in its entirety by reference thereto).

Nanostructures

As used in various embodiments, a nanowire is an elongated nanoscale semiconductor which, at any point along its length, has at least one cross-sectional dimension and, in some embodiments, two orthogonal cross-sectional dimensions less than 500 nanometers, preferably less than 200 nanometers, more preferably less than 150 nanometers, still more preferably less than 100 nanometers, even more preferably less than 70, still more preferably less than 50 nanometers, even more preferably less than 20 nanometers, still more preferably less than 10 nanometers, and even less than 5 nanometers. In other embodiments, the cross-sectional dimension can be less than 2 nanometers or 1 nanometer. In one set of embodiments the nanowire has at least one cross-sectional dimension ranging from 0.5 nanometers to 200 nanometers. Where nanowires are described having a core and an outer region, the above dimensions relate to those of the core. The cross-section of the elongated semiconductor may have any arbitrary shape, including, but not limited to, circular, square, rectangular, elliptical and tubular. Regular and irregular shapes are included. A non-limiting list of examples of materials from which nanowires of the invention can be made appears below.

Nanotubes are a class of nanowires that may find use in the invention and, in one embodiment, devices of the invention include wires of scale commensurate with nanotubes. As used herein, a "nanotube" is a nanowire that has a hollowed-out core, and includes those nanotubes know to those of ordinary skill in the art. A "non-nanotube nanowire" is any nanowire that is not a nanotube. In one set of embodiments of the invention, a non-nanotube nanowire having an unmodified surface (not including an auxiliary reaction entity not inherent in the nanotube in the environment in which it is positioned) is used in any arrangement of the invention described herein in which a nanowire or nanotube can be used. A "wire" refers to any material having a conductivity at least that of a semiconductor or metal. For example, the term "electrically conductive" or a "conductor" or an "electrical conductor" when used with reference to a "conducting" wire or a nanowire refers to the ability of that wire to pass charge through itself. Preferred electrically conductive materials have a resistivity lower than about $10^{-3}$, more preferably lower than about $10^{-4}$, and most preferably lower than about $10^{-6}$ or $10^{-7}$ ohm-meters.

Nanopore generally has one or more small holes in an electrically insulating membrane that can be used as a single-molecule detector. In some cases, it can be a biological protein channel in a high electrical resistance lipid bilayer or a pore in a solid-state membrane. Nanopore is generally a spherical structure in a nanoscale size with one or more pores therein. According to some aspects, a nanopore is made of carbon or any conducting material.

Nanobead is generally a spherical structure in a nanoscale size. The shape of nanobead is generally spherical but can also be circular, square, rectangular, elliptical and tubular. Regular and irregular shapes are included. In some examples, the nanobead may have a pore inside.

Nanogap is generally used in a biosensor that consists of separation between two contacts in the nanometer range. It senses when a target molecule, or a number of target molecules hybridize or binds between the two contacts allowing for the electrical signal to be transmitted through the molecules.

The foregoing nanostructures, namely, nanowire, nanotube, nanopore, nanobead, and nanogap are described to provide the instant illustration of some embodiments, and not for limiting the scope of the present invention. In addition to the foregoing examples, any nanostructure that has a nanoscale size and is suitable to be applied to nucleic acid detection methods and apparatus as disclosed in the application should also be considered to be included in the scope of the invention.

In general, sensing strategies for use with nanostructures or nanosensors to detect molecules and compounds is to sense changes in the charge at, or near their surfaces, or across a nanogap or nanopore, which cause a measurable change in their properties (such as field effect transistors, nanogaps, or piezoelectric nanosensors) to detect & quantify target nucleic acids (DNA, RNA, cDNA, etc).

Aspects of the invention provide a nanowire or nanowires preferably forming part of a system constructed and arranged to determine an analyte in a sample to which the nanowire(s) is exposed. "Determine", in this context, means to determine the quantity and/or presence of the analyte in the sample. Presence of the analyte can be determined by determining a change in a characteristic in the nanowire, typically an electrical characteristic or an optical characteristic. E.g. an analyte causes a detectable change in electrical conductivity of the nanowire or optical properties. In one embodiment, the nanowire includes, inherently, the ability to determine the analyte. The nanowire may be functionalized, i.e. comprising surface functional moieties, to which the analytes binds and induces a measurable property change to the nanowire. The binding events can be specific or non-specific. The functional moieties may include simple groups, selected from the groups including, but not limited to, —OH, —CHO, —COOH, —SO$_3$H, —CN, —SH, —COSH, COOR, halide; biomolecular entities including, but not limited to, amino acids, proteins, sugars, DNA, antibodies, antigens, and enzymes; grafted polymer chains with chain length less than the diameter of the nanowire core, selected from a group of polymers including, but not limited to, polyamide, polyester, polyimide, polyacrylic; a thin coating covering the surface of the nanowire core, including, but not limited to, the following groups of materials: metals, semiconductors, and insulators, which may be a metallic element, an oxide, an sulfide, a nitride, a selenide, a polymer and a polymer gel. In another embodiment, the invention provides a nanowire and a reaction entity with which the analyte interacts, positioned in relation to the nanowire such that the analyte can be determined by determining a change in a characteristic of the nanowire.

Field Effect Transistor (FET)

Field effect generally refers to an experimentally observable effect symbolized by F (on reaction rates, etc.) of intramolecular coulombic interaction between the centre of interest and a remote unipole or dipole, by direct action through space rather than through bonds. The magnitude of the field effect (or 'direct effect') may depend on the unipolar charge/dipole moment, orientation of dipole, shortest distance between the centre of interest and the remote unipole or dipole, and on the effective dielectric constant. This is exploited in transistors for computers and more recently in DNA field-effect transistors used as nanosensors.

Field-effect transistor (FET) is generally a field-effect transistor, which may use the field-effect due to the partial charges of biomolecules to function as a biosensor. The structure of FETs can be similar to that of metal-oxide-semiconductor field-effect transistor (MOSFETs) with the exception of the gate structure which, in biosensor FETs, may be replaced by a layer of immobilized probe molecules which act as surface receptors. When target biomolecules hybridize or bind, to the receptors, the charge distribution near the surface changes, which in turn modulates current transport through the semiconductor transducer (e.g. nanowire).

Biological Materials

The term sample or biological sample generally refers to any cell, tissue, or fluid from a biological source (a "biological sample"), or any other medium, biological or non-biological, that can be evaluated in accordance with the invention including, such as serum or water. A sample includes, but is not limited to, a biological sample drawn from an organism (e.g. a human, a non-human mammal, an invertebrate, a plant, a fungus, an algae, a bacteria, a virus, etc.), a sample drawn from food designed for human consumption, a sample including food designed for animal consumption such as livestock feed, milk, an organ donation sample, a sample of blood destined for a blood supply, a sample from a water supply, or the like. One example of a sample is a sample drawn from a human or animal to determine the presence or absence of a specific nucleic acid sequence.

The terms nucleic acid or oligonucleotide or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) Tetrahedron 49(10): 1925) and references therein; Letsinger (1970) J. Org. Chem. 35:3800; Sprinzl et al. (1977) Eur. J. Biochem. 81: 579; Letsinger et al. (1986) Nucl. Acids Res. 14: 3487; Sawai et al. (1984) Chem. Lett. 805, Letsinger et al. (1988) J. Am. Chem. Soc. 110: 4470; and Pauwels et al. (1986) Chemica Scripta 26: 1419), phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321, O-methylphophoroamidite linkages (see Eckstein, Oligonucleotides and Analogues: A Practical Approach, Oxford University Press), and peptide nucleic acid backbones and linkages (see Egholm (1992) J. Am. Chem. Soc. 114:1895; Meier et al. (1992) Chem. Int. Ed. Engl. 31: 1008; Nielsen (1993) Nature, 365: 566; Carlsson et al. (1996) Nature 380: 207). Other analog nucleic acids include those with positive backbones (Denpcy et al. (1995) Proc. Natl. Acad. Sci. USA 92: 6097; non-ionic backbones (U.S. Pat. Nos. 5,386,023, 5,637,684, 5,602,240, 5,216,141 and 4,469,863; Angew. (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghui and P. Dan Cook; Mesmaeker et al. (1994), Bioorganic & Medicinal Chem. Lett. 4: 395; Jeffs et al. (1994) J.

Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), Chem. Soc. Rev. pp. 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

Biosensors

As used in various embodiments, a biosensor is generally a device for the detection of an analyte that combines a biological component with a physicochemical detector component. In some embodiments, it may comprise three parts: 1. the sensitive biological element (biological material (eg. tissue, microorganisms, organelles, cell receptors, enzymes, antibodies, nucleic acids, etc), a biologically derived material or biomimic). The sensitive elements can be created by biological engineering; 2. the transducer or the detector element (works in a physicochemical way; optical, piezo-electric, electrochemical, etc.) that transforms the signal resulting from the interaction of the analyte with the biological element into another signal (i.e., transducers) that can be more easily measured and quantified; 3. associated electronics or signal processors that is primarily responsible for the display of the results in a user-friendly way. In some other embodiments, a biosensor may comprise a sample processing unit, a transducer unit, operably coupled to said sample processing unit, and a signal processing unit operably coupled to the conducting medium of the transducer unit. In some examples, the transducer unit may comprise a probe immobilized on a conducting medium, wherein the probe is prepared by amplifying the target nucleotide sequence and optionally at least one additional nucleotide sequence with one or more primers comprising a 5' anchor region, a 3' extension region, and a bubble region therebetween, wherein at least part of the 5' anchor region is removed after amplification as further described below. In some other examples, the signal processing unit may further comprise one or more of a signal sensing unit, a signal recording unit, a data processing unit, and a data reporting unit.

Sensing Strategies

In one aspect of the invention, a biological material configured to bind a nanostructure is a nucleic acid. Such nucleic acids may include DNA, RNA, and any derivatives thereof In one embodiment, the biological material is DNA. When DNA is attached to the nanostructure, the number of nucleotides may range from 5 bases to 100 bases. In some embodiments, the number of DNA nucleotides may be 7 bases, 10 bases, 15 bases, 20, bases, 25 bases, 30 bases, 35 bases, 40 bases, 45 bases, 50 bases, 60 bases, 70 bases, 80 bases, 90 bases and 100 bases. In some other embodiments, ribonucleic acids and any nucleic acid derivatives may be attached to the nanostructure. In still some other embodiments, DNA, RNA and its derivatives may be used simultaneously. Therefore in one example, DNA sequences may be attached to the nanostructure, whereas in another example, RNA sequences may be attached to the nanostructure, still another example, nucleic acid derivatives such as a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof may be attached to the nanostructure. In some other examples, nucleotide sequences comprising DNA and RNA, DNA and nucleic acid derivatives, RNA and derivatives, and DNA, RNA and derivatives may be attached to the nanostructure.

In another aspect of the invention, a nanostructure is conducting and can sense the electric charge at its surface, vicinity, inner tubes and/or the pores therein. One of key aspects of any diagnostic device is the ability to perform accurate detection of biomolecules with the performance determined by how well it detects specifically (i.e. a low false positive rate) and sensitively (i.e. a low false negative rate). Nanosensors that can sense changes in the charge at, or near their surfaces, or across a nanogap or nanopore, which cause a measurable change in their properties, at least in part due to the target molecule binding to a probe immobilized on or near the nanostructures, provide a method for ultra-sensitive detection without or with limited use of the need for labels (expensive chemicals that can be bound to the biomolecule or molecule of interest to enable detection devices to 'sense' them).

The present disclosure generally relates to molecular biological protocols and sensing strategies for use with nanosensors that may detect molecules and compounds by sensing changes in the charge at, or near their surfaces, or across a nanogap or nanopore, which cause a measurable change in their properties (such as field effect transistors, nanogaps, or piezoelectric nanostructures or nanosensors) to detect & quantify target nucleic acids (DNA, RNA, cDNA, etc). The basic function of these biosensors may require that a nucleotide polymer probe (or synthetic nucleotide polymer such as PNA, Morpholinos, etc) be immobilized on, or near to, the nanostructures and the build up of target molecules binding to the probe can cause an increase in charge density at or near the surface of the nanostructures or nanosensors, due to the charge of the probe. For instance, an amplified PCR fragment binding to a probe (with a reverse complimentary sequence to the target nucleotide polymer), immobilized on a nanowire can cause a measurable change conductance ($\Delta G$) due to the increase in negative charge at, or near to the nanowire's surface, due to a phenomena called the field effect.

These nanosensors may offer the potential for sensitive and dynamic detection of biomolecules, however, this sensitivity may bring with it a number of issues. For instance, natural fluctuations of charge at the surface, within the sample matrix may cause noise, in part due to the flanking sequences of target nucleotide polymer molecules (i.e. the over hanging sequences that don't bind to the probes). Furthermore, if many target molecules are being detected at the same time on an array of nanosensors, it would be favorable to standardize the size and therefore charge mass, of each of these molecules to allow for more stringent comparisons and quality control. Moreover, having a standard size for all target molecules allows for standardization of probe hybridization conditions in the array assay design.

Some aspects of biological protocols presented herein may enhance the nanosensors to provide sensitive and specific detection and describe methodologies wherein target nucleic acids can be enzymatically processed to remove flanking sequences (defined as sequenced that may not bind to the detection probes), or amplified using novel primers that may allow for the consistent & specific amplification of short fragments, wherein the primers may contain restriction enzyme sites for removal of the majority of the primers from the amplicons, to ensure clear cut, reproducible detection and quantification signals as the target molecules may be uniform in size and may not have, or may have short, flanking sequences.

Flanking sequences from hybridised target nucleotide polymer molecules can be, by definition, in close proximity to the nanostructures or nanosensors and may therefore contribute a measurable effect that might overload the signal from the hybridisation. Moreover, this flanking sequence can also increase the risk of non-specific hybridisation, dimer formation and steric hindrance at, or near the nanostructures, which might also affect the nanostructure signal. By removing long flanking sequences arrayed nanostructures can be positioned closer to each other, effectively increasing the density of the array features, the hybridization assay conditions are standardized, the signal from all the targets will be the same and background signals from flanking sequences removed.

Embodiments presented herein provide both methods of removing this flanking sequence and it's advantages for the detection of biomolecules using nanosensors that may sense changes in the charge at, or near their surfaces, or across a nanogap or nanopore, which may cause a measurable change in their properties, due to the target molecule binding to a probe immobilized on or near the nanostructures or nanosensors.

Biosensor is generally an analytical device that may convert molecular events into electrical signals. The nanostructures used in a biosensor are generally used to detect components of interest such as nucleic acids. Biosensors can generally operate in the liquid or gas phase, opening up an enormous variety of applications, e.g., for integrated devices and for downstream applications. Therefore, the biosensors can be manufactured inexpensively and portable and are optionally used as implantable detection and monitoring devices. Alternatively, the biosensor can be coupled with other high-resolution apparatus such as mass-spectroscopy and provide further information including the detection of presence, abundance and/or structural variation of the target biomolecules.

One aspect of the invention involves a sensing element of a biosensor, which can be an electronic sensing element, and a nanowire able to detect the presence, or absence, of an analyte in a sample (e.g. a fluid sample) containing, or suspected of containing, the analyte. Nanoscale sensors of the invention may be used, for example, in chemical applications to detect pH or the presence of metal ions; in biological applications to detect a protein, nucleic acid (e.g. DNA, RNA, etc.), a sugar or carbohydrate, and/or metal ions; and in environmental applications to detect pH, metal ions, or other analytes of interest.

Another aspect of the invention involves an article of a biosensor comprising a sample exposure region and a nanowire able to detect the presence of absence of an analyte. The sample exposure region may be any region in close proximity to the nanowire wherein a sample in the sample exposure region addresses at least a portion of the nanowire. Examples of sample exposure regions include, but are not limited to, a well, a channel, a microchannel, and a gel. In preferred embodiments, the sample exposure region holds a sample proximate the nanowire, or may direct a sample toward the nanowire for determination of an analyte in the sample. The nanowire may be positioned adjacent to or within the sample exposure region. Alternatively, the nanowire may be a probe that is inserted into a fluid or fluid flow path. The nanowire probe may also comprise a micro-needle and the sample exposure region may be addressable by a biological sample. In this arrangement, a device that is constructed and arranged for insertion of a micro-needle probe into a biological sample will include a region surrounding the micro-needle that defines the sample exposure region, and a sample in the sample exposure region is addressable by the nanowire, and vice-versa. Fluid flow channels can be created at a size and scale advantageous for use in the invention (microchannels) using a variety of techniques such as those described in International Patent Publication No. WO 97/33737, published Sep. 18, 1997, and incorporated herein by reference.

In another aspect of the invention, an article may comprise a plurality of nanowires able to detect the presence or absence of a plurality of one or more analytes. The individual nanowires may be differentially doped as described above, thereby varying the sensitivity of each nanowire to the analyte. Alternatively, individual nanowires may be selected based on their ability to interact with specific analytes, thereby allowing the detection of a variety of analytes. The plurality of nanowires may be randomly oriented or parallel to one another. Alternatively, the plurality of nanowires may be oriented in an array on a substrate.

Where a detector is present, any detector capable of determining a property associated with the nanowire can be used. The property can be electronic, optical, or the like. An electronic property of the nanowire can be, for example, its conductivity, resistivity, etc. An optical property associated with the nanowire can include its emission intensity, or emission wavelength where the nanowire is an emissive nanowire where emission occurs at a p-n junction. For example, the detector can be constructed for measuring a change in an electronic or magnetic property (e.g. voltage, current, conductivity, resistance, impedance, inductance, charge, etc.) can be used. The detector typically includes a power source and a voltmeter or amp meter. In one embodiment, a conductance less than 1 nS can be detected. In a preferred embodiment, a conductance in the range of thousandths of a nS can be detected. The concentration of a species, or analyte, may be detected from less than micromolar to molar concentrations and above. By using nanowires with known detectors, sensitivity can be extended to a single molecule. In one embodiment, an article of the invention is capable of delivering a stimulus to the nanowire and the detector is constructed and arranged to determine a signal resulting from the stimulus. For example, a nanowire including a p-n junction can be delivered a stimulus (electronic current), where the detector is constructed and arranged to determine a signal (electromagnetic radiation) resulting from the stimulus. In such an arrangement, interaction of an analyte with the nanowire, or with a reaction entity positioned proximate the nanowire, can affect the signal in a detectable manner. In another example, where the reaction entity is a quantum dot, the quantum dot may be constructed to receive electromagnetic radiation of one wavelength and emit electromagnetic radiation of a different wavelength. Where the stimulus is electromagnetic radiation, it can be affected by interaction with an analyte, and the detector can detect a change in a signal resulting therefrom. Examples of stimuli include a constant current/voltage, an alternating voltage, and electromagnetic radiation such as light.

Another aspect of the present invention provides an article comprising a nanowire and a detector constructed and arranged to determine a change in an electrical property of the nanowire. At least a portion of the nanowire is addressable by a sample containing, or suspected of containing, an analyte. The phrase "addressable by a fluid" is defined as the ability of the fluid to be positioned relative to the nanowire so that an analyte suspected of being in the fluid is able to interact with the nanowire. The fluid may be proximate to or in contact with the nanowire.

In some embodiments, the nanostructures can be assembled into a plurality of parallel arrays such as microcolumns at higher densities than is and in a format compatible with currently available micro-fluidic systems. The nanostructure arrays optionally comprise a plurality of nanostructures such as nanowires, nanotubes, nanopores, nanobeads, nanogaps, or a combination thereof. Each nanostructure of the array can be electrically connected, e.g., via two or more electrodes to a battery for applying a voltage across the nanowire and a detector, for detection of any changes in conductance of the nanowire. Alternatively, each nanostructure separately receives electricity or only a portion of nanostructures arrayed together may be electrically connected.

A single detector or a combination of detectors is optionally used to detect the signal from the array of nanowires. For example, each nanowire linked to a probe comprising different target sequence, which may be bound to a same or different probe, is optionally detected separately, such that a spatial array of a plurality of nanowires can be used to quickly identify, e.g., a plurality of different nucleotide sequences present in a biological sample such as blood. In some examples, a plurality of patches of nanostructures are prepared in the array and each patch presents different probes to detect multiple target sequences in a biological sample. Alternatively, in some other examples, an entire nanostructures present in the array may present same probes, thereby only one target sequence would be tested for its presence, abundance and/or variation in the sequence.

The detection by the nanostructure or nanosensor is generally a change in conductance of the nanostructure or of its environment. The signal can be expressed in terms of a change in the voltage across the nanostructure, or the current through the nanostructure. Such changes are typically detected electrically, e.g., with a voltmeter and/or a current meter. Alternatively, the signal is detected digitally. In one embodiment, a voltage is applied across a nanostructure, e.g., a nanowire, providing a steady state signal. When a binding event occurs on the probe attached to the nanostructure, the electric field in the vicinity of the nanostructure changes and the conductance of the nanostructure changes, producing a fluctuation or shift in the steady state signal. The signal may be detected, electrically or digitally, and provides real time detection of the event of interest.

Biosensor can also be integrated into a system for detecting a presence, level and/or variation of biomolecules. In one aspect, such system may include an electrical power supply, monitoring system for applying and measuring electrical current across the nanostructure element. In another aspect, such system may further include data processing capabilities to enable the programmed operation of the nanostructures and to receive, store, and provide useful analysis and display of the data that is obtained. In addition a computer system to process the obtained data as well as additional processor(s) may be integrated into a biosensor system if desired. The computer system or any additional elements present in a biosensor system may provide a software(s) for analyzing the data or for automatic operation and/or manual(s) to perform detection processes with a biosensor. Furthermore, any additional elements that may enhance the performance of a biosensor system can be added.

A biosensor of the present invention can collect real time data. The real time data may be used, for example, to monitor the reaction rate of a specific chemical or biological reaction. Physiological conditions or drug concentrations present in vivo may also produce a real time signal that may be used to control a drug delivery system. For example, the present invention includes, in one aspect, an integrated system, comprising a nanowire detector, a reader and a computer controlled response system. In this example, the nanowire detects a change in the equilibrium of an analyte in the sample, feeding a signal to the computer controlled response system causing it to withhold or release a chemical or drug. This is particularly useful as an implantable drug or chemical delivery system because of its small size and low energy requirements. Those of ordinary skill in the art are well aware of the parameters and requirements for constructing implantable devices, readers, and computer-controlled response systems suitable for use in connection with the present invention. That is, the knowledge of those of ordinary skill in the art, coupled with the disclosure herein of nanowires as sensors, enables implantable devices, real-time measurement devices, integrated systems, and the like. Such systems can be made capable of monitoring one, or a plurality of physiological characteristics individually or simultaneously. Such physiological characteristics can include, for example, oxygen concentration, carbon dioxide concentration, glucose level, concentration of a particular drug, concentration of a particular drug by-product, or the like. Integrated physiological devices can be constructed to carry out a function depending upon a condition sensed by a sensor of the invention. For example, a nanowire sensor of the invention can sense glucose level and, based upon the determined glucose level can cause the release of insulin into a subject through an appropriate controller mechanism.

Primers

One embodiment used in connection with the present disclosure describes a novel primer design that may allow for short sequence amplification and subsequent restriction enzyme 'cropping' to provide short amplified target sequences. Such novel primer design and processing method can be applied not only for the preparation of probes but also for analytes, which comprise a target nucleotide sequence and optional additional sequences attached to the target sequence. Moreover, in some embodiments, the probes as well as the analytes both are prepared with the novel primer design and cropping processing to increase the detection accuracy of a biosensor. As also disclosed elsewhere in the specification, the preparation and/or processing of probes and analytes according to the novel primer design and cropping processing can be done before they are provided into a biosensor or actually can be done in the biosensor. For the purpose of instant illustration, some non-limiting examples of the foregoing applications are presented in the following Examples section.

Another embodiment describes a method to enzymatically removing unhybridized, and therefore, single stranded target nucleotide polymer sequence by using nuclease enzymes that may specifically catalyse the break down of single stranded nucleotide polymers to their constituent monomers, nucleotides, and methods of using this process to provide highly sensitive and reproducible multiplexing. Also, for an instant illustration, some non-limiting examples of this application are presented in the following Examples section.

EXAMPLES

Example 1

Novel Probe Design to Enable Consistent Short Amplicons and Amplified Primer Cropping Generally, in molecular biology nucleotide polymer sequences of interest have been studied by amplifying specific regions of genomes, or other nucleotide polymers such a RNAs, cDNAs, etc using a method called the polymerase chain reaction. This method often requires that two primers (short oligonucleotides) be synthesised with the reverse compliment sequence of sequences of interest within target nucleotide polymer molecules, that flank the sequence of interest (for instance a Single Nucleotide Polymorphism, or repeat, etc). These primers are added to the target molecule, along with a polymerase (an enzyme that catalyses the polymerization, from a template sequence, of nucleotides into a nucleotide polymer. In PCR special thermal stable polymerases are used, such as Taq polymerase from the thermophilic bacterium Thermus aquaticus, which has an optimum temperature for activity of 75-80° C.), nucleotide monomers (Adenine, Guanine, Cytosine and Thymine) and buffers to allow for polymerase action. The mix is heated to 92-94° C. which melts (i.e. causes the hydrogen bonding between two chains of complimentary nucleotide polymer chains to break) and is then rapidly cooled to the melting temperature of the oligonucleotide primers, which allows for them to hybridise to the target molecule. The mix is then rapidly heated up to 72° C., which is the optimum temperature for Taq Polymerase catalysis and the enzyme 'fills in' the gap between the two primers, therefore creating another copy of the nucleotide polymer between the two primers. This thermal cycling is repeats to produce two more copies and then again to produce four more copies, and so on, until the number of copies is at a detectable level. Other methods of amplifying specific sequences from target nucleotide polymer molecules include the isothermal methods of HDA, RPA, LAMP, etc.

In general, primer design however, can be complex and highly sequence dependent. It is often difficult to consistently amplify short nucleotide polymer sequences as good traditional 'primer sites' (i.e. sites within a nucleotide polymer molecule that have a sequence that is suitable for primers to bind) might not be available directly adjacent to the sequence of interest in the target molecule. Furthermore, the primers themselves can be included in the amplicon, and this may mean an extra 18 or more nucleotides both 5' and 3' of the target sequence. Some illustrative examples of the present disclosure describe a method of designing primers that consistently may allow for short amplifications and a method of removing some primer sequence in the final amplicon.

In some embodiments, the primers described in this particular example comprise at least three separate continuous sections within a single oligonucleotide molecule: (1) a 5' anchor section that attaches the primer to the specific region of the target molecule, (2) a 3' 'extension' region which comprises a short sequence, about 8-15 by long, but can be up to 15 by or more, with a low Tm (optimized to only hybridize under selective conditions when the anchor region is hybridized), which may act as the start site for polymerization, and (3) a 'bubble' region that is about 50% or less complementary to the target sequence. In some embodiments, one or more nucleotide sequences that can be cleavable by a nuclease may be present in the 5' anchor region and/or the bubble region.

The 'anchor' section, located at the 5' of the oligonucleotide sequence can be designed to be between 15-30 bp, although can be shorter with a high GC content, or longer if required, and in some embodiments, is 100% complementary to the target sequence, but can also be between about 70-100% complementary to the target sequence that it is to bind to. In some embodiments, the length of the 5' anchor region can be variable so that it can be about 15-30 bp, 15-25 bp, or 15-20 by in various examples. Unlike some other primer design methods, this section does not have to be fully homologous to the target sequence. It is called the anchor as it can initially anchor the primer to the target molecule.

The 'extension' section can be located at the 3' end of the primer and can be designed to also be, in some examples, fully, or nearly fully reverse complimentary to the target sequence. The length of 3' extension region can also be variable, such that it can be about 5-30 bp, 5-25 bp, 5-20 bp, 5-15 by 5-12 bp, or 5-10 by in various examples. The melting temperature Tm of this region may be important as it can be low to allow binding once the anchor region has hybridised. Thus the thermodynamics of the system and PCR conditions will only allow the 'extension' section to hybridize to the target molecule if the match is fully, or at least nearly fully, complimentary.

The melting temperature (Tm) as used in some embodiments herein is the temperature at which the hydrogen bond that may bind two strands of nucleotide polymers together, such as in DNA duplexes, break resulting in two single stranded nucleotide polymer molecules. The melting temperature may depend upon length (i,e, number of nucleotide monomers in the polymer that can hydrogen bond), salt concentration and nucleotide polymer sequence composition (Guanine and Cytosine hydrogen bond with each other with three hydrogen bonds and Thymine and Adenine exclusively bond with each other with two hydrogen bonds, so high CG duplexes have a higher Tm than high AT duplexes). The following equation provides a useful estimation of Tm:

$$Tm = 16.6 \times \log Cs + 0.41 \times (\% G+C) + 81.5 - 820/L$$

where C is salt concentration and L is length of duplex. (Schildkraut, C. & Lifson, S. 1965—Biopolymers 3, 195-208; Thomas, C. A. Jnr. & Dancis B. M. 1973—Journal of molecular biology, 77, 43-55)

The 'bubble' region is the internal section between the 'anchor' and the 'extension' region. It may or may not be complimentary, or in some embodiments can be partly complimentary, or in other embodiments contains no matching base pairs with the target sequence and consists of about 2-10 unmatched nucleotides. In some embodiments a universal base (such as inosine) is the 3' most base pair, which helps to create the bubble. Due to the sequence of the nucleotides in the polymer chain not matching, or partly matching the target molecule sequence, it can form a 'bubble', or area of unhybridized nucleotide polymer. Due to the thermodynamics of this bubble, the design of the primer may require that the 'extension' may match the respective region in the target molecule, in certain embodiments, 100% to allow it to bind and therefore allow for the polymerase to act and proceed with polymerization. Furthermore, it may require that parts of the bubble section match in part, or that the anchor section is longer to counter the mismatched bubble section.

In part, as the 'anchor' section is not required to be fully complimentary and the thermodynamics of the 'bubble' and 'extension' regions, primers can consistently be designed, in certain aspects of embodiments, directly adjacent to the sequence of interest in the target molecule, primer sets can be designed to allow for short target sequences to be amplified and in multiplex as there primer dimerization is not observed with these primers.

Once the amplification process is performed, the amplified target sequences can be cropped, to remove the two 'anchor' regions and/or bubble regions, further reducing the size of the target sequences to be detected on the biosensors described above.

The above-described primer structure allows for less stringent primer design. As the anchor is long it hybridizes to the template easily, however, the non-hybridizing bubble isolates the extension region, which therefore must have a near perfect match to the sequence to bind, as the thermodynamics require almost 100% homology. For instance, we can design the primers so that the SNP of interest is at or near the 3' end. Therefore the Wild Type sequence will allow extension and therefore amplification, but the mutant type will not allow it, as the extension region won't hybridize to allow for extension. These thermodynamics mean that large numbers can be multiplexed (e.g., up to 100 plex in a single tube) and not be too fussy about where the primers are placed, thus enabling one to ensure consist design for short amplicons.

Figure 1:
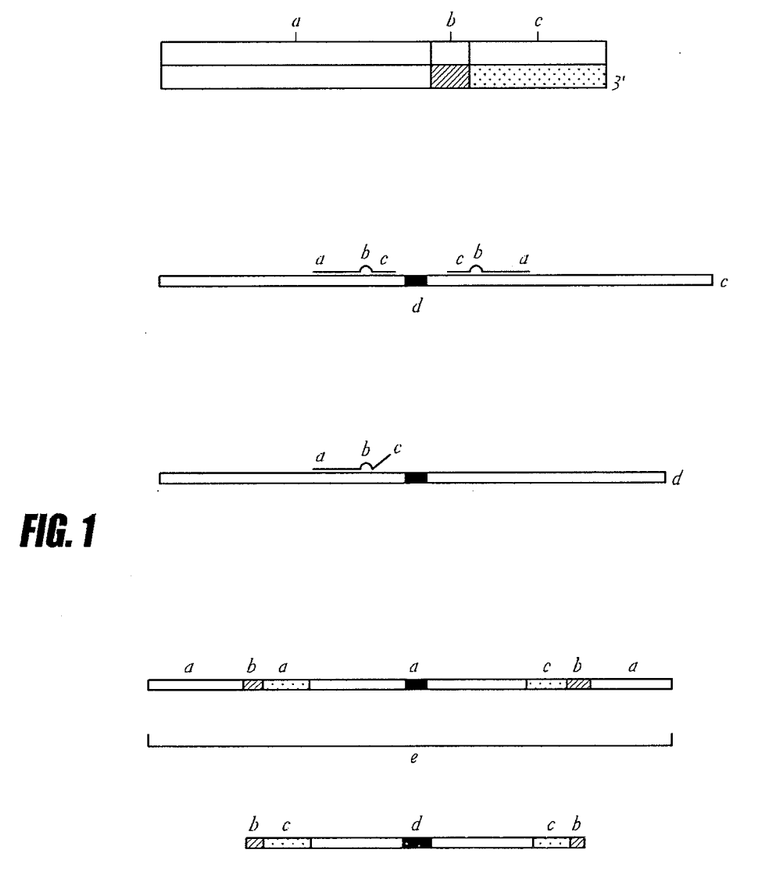
FIG. 1 provides an illustrative embodiment of novel probe design.

Some non-limiting illustrations of the foregoing particular Example 1 are presented in FIG. 1. With reference to FIG. 1:

i) illustrates the topology of the primers described in some embodiments. 'a' represents the 'anchor' section, 'b' represents the 'bubble' region and 'c' represents the 'extension' region.

ii) illustrates two primers hybridized successfully adjacent to the sequence of interest, 'a' represents the 'anchor' section, 'b' represents the 'bubble' region and 'c' represents the 'extension'.

iii) illustrates a situation wherein the 'anchor' region had hybridized, by the 'extension' region has yet to bind. This could be for one of several reasons; 1. the temperature has yet to come down to a point that may facilitate hybridization of the extension region, 2. the sequence in the 'extension' region may not perfectly reverse compliment to the respective sequence in the target sequence. This might be due to the 'anchor' region binding to a repeat sequence, or a close match, but due to the thermodynamics of the bubble and extension regions, the extension's region may need to be a 100% match for it to hybridise at least in some examples.

iv) illustrates the topology of an amplicon, amplified using this primer system. 'a' represents the 'anchor' section, 'b' represents the 'bubble' region, 'c' represents the 'extension' region and 'd' represents the sequence of interest.

v) represents the topology of the amplicon following restriction enzyme digestion.

Example 2

Preparation of Analytes Using a Novel Primer Design and Amplified Primer Cropping A similar method used to prepare probes, which is described in Example 1, can also be employed to prepare analytes in some embodiments. The analytes prepared by such procedures would comprise target nucleotide sequence(s) and part of primer sequences and would not contain additional sequences, which may be added via PCR errors or random mismatching of the primers. Therefore, the signal of the nucleic acid detection would be mainly determined by the target sequences and would not be influenced by the presence of additional non-target sequences. As such, at least in some embodiments, the accuracy of the detection would be improved.

Example 3

Nuclease Processing of Analytes

A nuclease is an enzyme capable of cleaving the phosphodiester bonds between the nucleotide subunits of nucleic acids. Some nucleases can recognize and cleave specific sequences, whereas some other nucleases can cleave nucleotide polymers without preference to certain nucleotide sequences. Sequence-specific nucleases generally include a variety of restriction enzymes that are readily available in the art. Sequence-nonspecific nucleases are also available in the art and some examples of them are S1 nuclease, P1 nuclease, micrococcal nuclease, mung bean nuclease, exonuclease, II, III, IV, V, VI, VII and VIII, and Klenow fragment. In various embodiments of the present invention, such sequence-specific and sequence-nonspecific nuclease are all included and also the nuclease specific to DNA, RNA or both are also included. In certain some embodiments, a nuclease that can cleave a single stranded nucleic acid only can be used to process analytes. In the following example, using S1 nuclease as a non-limiting example, some embodiments of the invention are further described.

Single stranded DNA specific nuclease enzyme activity was first observed in cell free extracts of *Escherichia coli* in 1960, by I. R. Lehman and later in cells of *E. coli* infected with a phage (S. Bose & N. Nossal, 1964), and in snake venom (I. L. Nikolskaya, et. al. 1964). The *E. coli* phosphodiesterase exhibits a low order of enzymatic activity with intact double stranded DNA as a substrate, which is due to the enzymes inability to catalyse an extended, hydrogen bonded, double stranded DNA structure.

S1 nuclease, which specifically splits the phosphodiester-bond of ssDNA, is commercially available from most suppliers of molecular biology reagents (Sigma, Fermentas, etc). The commercially sold variant is usually the Si nuclease isolated from *Aspergillus oryzae* (T. Ando, 1965). The enzyme is a 29 kd glycoprotein with carbohydrate content of 18%.

The enzyme can be more active in the presence of $1 \times 10^{-4}$ M $Zn^{2+}$ and less active in the presence of an equal amount of RNA, with one unit of the enzyme producing 1 μg of acid soluble deoxyribonucleotides in 1 min at 37° C. Again, the reaction buffer is commercially available—200 mM sodium-acetate (pH 4.5 at 25° C.), 1.5 M NaCl and 10 mM $ZnSO_4$ (Fermentas). The digestion products from a denatured DNA can be identified as 5'-deoxynucleotides.

In general, detection of nucleotide polymers may rely on the target molecules that can be sheered, expressed or amplified, with or without consideration as to the length of the target molecules, hybridizing to probes and detection provided by binding another fluorescent probe to this complex (for instance a antibody conjugated with a fluorescent moiety which is detected optically). For some detection systems, this can generally be acceptable as the fluorescence reporting methodologies may not be affected by the extra, non-hybridized flanking sequences. However, when detecting nucleotides using nanosensors that can exploit changes in electrical properties in part due to hybridization events, the flanking sequence can be important as it may carry an electrical charge that can affect the signal from the biosensor. One example of some embodiments proposes methods for the processing of target sequences that can be derived, for example, by being sheered or enzymatically fragmented, expressed or amplified into 'target' DNA molecules containing the specific region of interest.

This, in one embodiment, can be achieved by the nuclease (such as S1 nuclease) digestion of the single stranded flanking sequence not hybridized to probes, in situ, following hybridization of target nucleotide polymers. By reducing the size of the target molecules we may allow the system to be more sensitive and can more readily differentiate between different concentrations of target molecule enabling quantitative analyses of target nucleic acid species.

In one embodiment, once nuclease digestion of the flanking sequence is performed, this 'cropped' target molecule can then be 'melted' by increasing the temperature to release it to allow it to then be detected by the biosensor, or if the probe is already immobilized on the biosensor, a measurement can be taken.

In some illustrative embodiments, once nuclease digestion of the flanking sequence is performed, this 'cropped' target molecule can then be 'melted' by increasing the temperature to release it to allow it to then be detected by the nanosensor, or if the probe is already immobilized on the nanosensor, a measurement can be taken.

Figure 2:
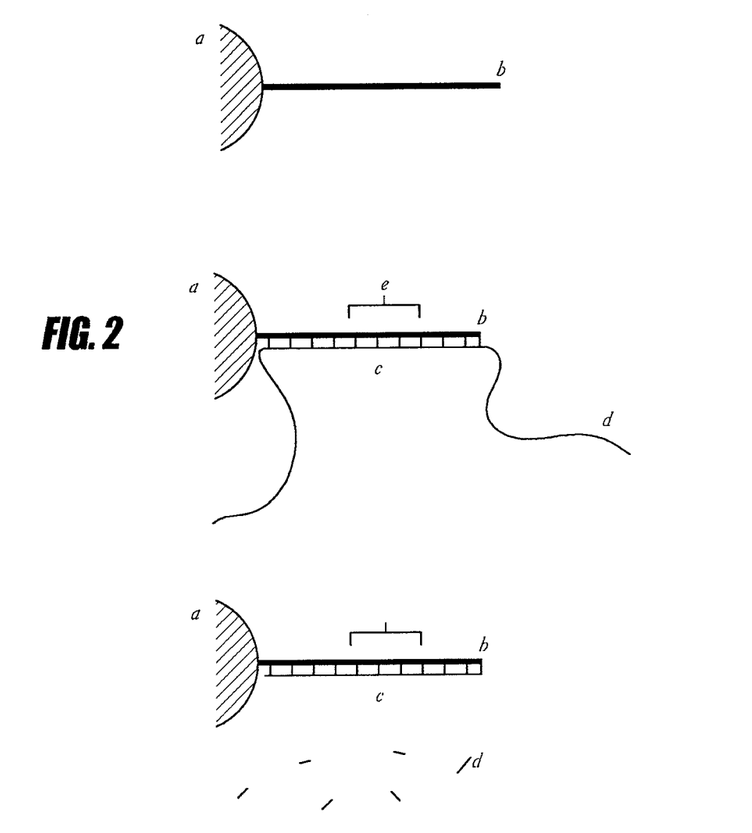
FIG. 2 provides an illustrative embodiment of Si Nuclease processing of nucleic acids.
Figure 3:
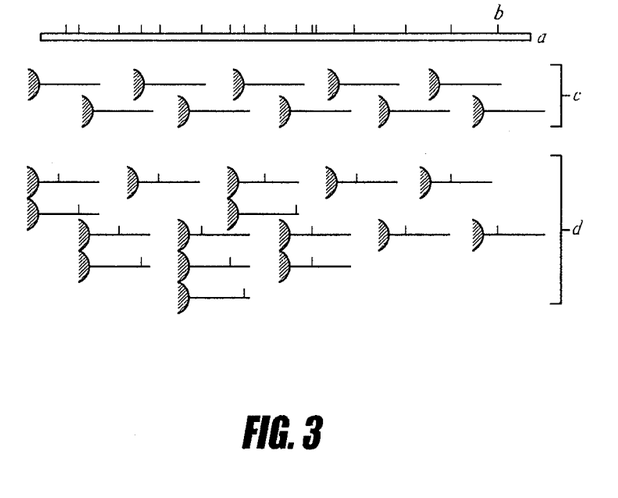
FIG. 3 is an illustrative embodiment of an experimental design of a multiplex detection reaction.

Some illustrations of the foregoing particular Example 3 are presented in FIGS. 2 and 3. With reference to FIG. 2,
i) illustrates a probe, b, immobilized on a solid support, a, this might be the biosensor (for example, but not limited to, a nanowire, or carbon nanotube), a nanoparticle (such as, but not limited to, a nanosphere or microbead), or any other solid support.
ii) illustrates a target nucleotide polymer, c, that can be derived by being sheered or enzymatically fragmented, expressed or amplified, bound to the probe attached to the solid support, a. Note that, in this particular illustration of some embodiments, only the duplexed region contains the specific sequence of interest and that the flanking sequence remain single stranded.
iii) this diagram illustrates what may remain after digestion with a nuclease (such as S1 nuclease), i.e. only the target sequence at least in this particular illustration, c, that was duplexed with the probe and nucleotide monomers, d. This 'cropped' target molecule can then be 'melted' by increasing the temperature to release it to allow it to then be detected by the biosensor, or if the probe is already immobilized on the biosensor, a measurement can be taken. In FIG. 2, the target sequence contains allelic or mutation loci or a specific sequence of interest, e.

Example 4

Detection of Multiple Target Nucleotide Sequences (Multiplexing)

Furthermore, in some other embodiments, multiplex detection of many sites within target sequences can be possible by tiling probes to interrogated these multiple sites on a target sequence or in multiple target sequences. In this particular example, the target sequence might contain several known mutations and can be derived by being sheered or enzymatically fragmented, expressed & reverse transcribed or amplified. In one embodiments, overlapping tiling probes can generally be designed each to have the same, or similar Tm's, to cover the wild-type sequence. Furthermore, in certain embodiments, 'mutation' or 'species specific' or 'sequence of interest specific' probes can generally be designed one probe per mutation, or per species specific sequence, or per haplotype/allele/or sequence of interest, with the same or similar Tm's as the wild-type probes.

Each probe may bind to a sheered or enzymatically fragmented, expressed & reverse transcribed or amplified copy of the target sequence and, once hybridised at the probes Tm, digested with nuclease to leave, in one example, only the duplexed the sequence. Mismatches, for instance if a mutant probe can bind non-specifically to a wild type target sequence may be eliminated by titrating the experimental conditions to prevent such non-specific binding (for instance, altering the salt concentration, the temperature, or using PNAs as the probes as PNA/DNA)

With reference to FIG. 3,
i) illustrates one possible experimental design of a multiplex detection reaction that may enable a single long amplicon to be interrogated by shorter probes. In this case, the target sequence a, BRCA exon 10, which may contain 16 known mutations, b, can be derived by being sheered or enzymatically fragmented, expressed & reverse transcribed or amplified. Overlapping tiling probes can be designed each to have the same, or similar Tm's, to cover the wild-type sequence, c. Furthermore, 'mutation' probes can be designed, d, one probe per mutation, with the same or similar Tm's as the wild-type probes. Each probe may bind to an amplified copy of the target sequence and, once hybridized at the probes Tm, digested with nuclease to leave the duplexed the sequence. Mismatches, for instance if a mutant probe binds non-specifically to a wild type target sequence maybe eliminated by titrating the experimental conditions to prevent such non-specific binding (for instance, altering the salt concentration, the temperature, or using PNAs as the probes as PNA/DNA complexes may be less stable that DNA/DNA complexes and mismatches within non-specific binding events may be accessible by nuclease and can be removed.

Example 5

Detection of Analytes with a Biosensor-I

From Example 5 to 7, for the purpose of illustration of some embodiments, methods of detecting sequence variations in a human adenomatous polyposis coli gene are described. This illustration is provided only to more expressly explain some embodiments of the presently disclosed methods and should not be considered to limit the scope of the invention. As also disclosed in elsewhere in the specification, various detection methods presented in this application can be applied to a variety of purposes including, but not limited to, prognosis, prediction and/or diagnosis of certain diseases in a mammal including humans as well as detection of some pathogens such as bacteria, virus and fungi in liquid, gas or any environment of interest.

Mutation of human adenomatous polyposis coli (APC) gene, especially somatic mutations of this gene in colon tissues has been well implicated in tumor budding and/or colorectal cancer. For example, the research publication by Jass et al (Journal of Clinical Pathology 2003; 56: 69-73) lists the somatic mutation bases in the gene and its correlated type of colorectal cancer. As such, it would be desirable to detect if any of such cited mutations in APC gene is present in an individual to evaluate the current health status and also a potential risk of colon cancer. For example, if MSI-H type of colon cancer is concerned, which is related to the mutation in codon no. 1295 of APC gene, the following procedures may be practiced.

1. Sample collection: To determine somatic mutation of APC gene in an individual, some colon tissues can be obtained by a variety of methods available in the art such as a surgical incision and collection. In some cases, a biosensor may comprise a unit/element configured to collect samples. Alternatively the sample may be collected by separate equipment.

2. Analyte preparation: Once the colon tissue is obtained, the genomic DNA of the tissue can be obtained also by a variety of methods present in the art such as an alkaline lysis extraction method of DNA. In some cases, a biosensor may comprise a unit/element configured to prepare analytes, whereas in some other cases, the preparation of analytes may be done separately and the prepared analytes may be provided to a biosensor.

In one example (Example 5A), the genomic DNA may be obtained and further fragmented to be suitable to hybridize with the probes via physical methods and/or chemical methods. Physical methods of DNA fragmentation may include, but not limited to, sonication of DNA. Chemical methods of DNA fragmentation may include, but not limited to, restriction with nucleases. In some embodiment, the physical and chemical methods can be applied to the genomic DNA together.

In another example (Example 5B), using specific primers to the target region of the APC gene, amplification of the target nucleotide sequence can be performed. In some cases, the primers used in this amplification may comprise a 5' anchor region, a 3' extension region and a bubble region as described in elsewhere in the specification. Once the analyte comprising the target region of the APC gene and primer sequences is obtained from the amplification reaction (e.g. PCR), it can be treated with a certain nucleases to remove at least part of the primer sequences. Such embodiments would be desirable if one or more nuclease recognition sequence(s) are present in the 5' anchor region and/or the bubble region of the primers. In some other cases, however, the primers may not comprise one or more of the 5' anchor region, a 3' extension region and a bubble region and may not be cleaved with nucleases. In such cases, the amplified analytes may proceed to the hybridization with the probes without nuclease treatment.

3. Probe preparation: According to the methods as disclosed in Example 1, the probes specific to the target region of the human APC gene can be prepared in this particular example. The primers used for this probe preparation may comprise a 5' anchor region, a 3' extension region and a bubble region and one or more of nuclease cleavage sites may present in the 5' anchor region and/or the bubble region. Once the target sequences are amplified with the specific primers, at least part of the primer sequences can be removed by nuclease treatment. As such, the resulting target sequences, which will be used as probes, can be substantially consistent in size. The prepared probes can be linked to nanostructures/nanosensors (e.g. nanowires, nanotubes, nanobeads, nanopores, nanogaps and others) by a variety of methods available in the art. If more than one types of colon cancer wish to be tested, multiple kinds of probes (i.e. probes specific to different target regions of the APC gene) may be prepared and linked to the nanosensors. In some cases, a biosensor may comprise a unit/element configured to prepare probes, whereas in some other cases, the preparation of probes may be done separately and the prepared probes may be provided to a biosensor.

4. Hybridization: The analytes prepared as in Example 5A or 5B can be provided to the array of nanostructures/nanosensors comprising the probes. Such hybridization may occur in a liquid condition or gas condition. As disclosed in elsewhere in the specification, the recruitment of the target sequence to the probe can cause changes in the charge at, or near their surfaces, or across the nanostructures. Stringency of hybridization between the probes and the target sequences (having sequence variations in some cases) can be controlled by manipulating various factors such as pH, salt concentration, and/or temperature of the reaction environment. Once the signals are sensed individually or collectively from the plurality of nanostructures, these signal data can be further processed if desired. In some cases, a biosensor may comprise a unit/element configured to perform the hybridization. In certain some examples, this hybridization unit is operably coupled to other unit/elements such as a sample collection unit, a sample preparation unit and/or a probe preparation unit.

5. Data processing: Depending on the experimental settings, a variety of kinds of data, indicating, for example, the presence of certain mutation allele(s) of the APC gene in the test individual, the abundance of the certain mutation allele(s) of APC in the individual and the determination of specific mutation(s) of APC in the tested individual, can be obtained. In some cases, a biosensor may comprise a unit/element configured to process data obtained from the nanostructures. In certain some examples, this data processing unit is operably coupled to other unit/element(s) of a biosensor, or alternatively can be separately operated.

6. Generation of report: Once the detection data are processed and desired results are obtained (e.g. presence and/or abundance of concerned APC mutations and its corresponding cancer type), such information may be generated in a form of report to provide a medical practitioner and/or the tested individual. In some cases, the biosensor may comprise a unit/element configured to generate a report obtained from the nanostructures/nanosensors. In certain some examples, this report generation unit is operably coupled to other unit/element(s) of a biosensor, or alternatively can be separately operated.

Example 6

Detection of Analytes with a Biosensor-II

Example 6 presents another embodiment of the present invention using an illustrative scenario of human APC gene detection.

1. Sample collection: To determine somatic mutation of APC gene in an individual, some colon tissues can be obtained by a variety of methods available in the art such as a surgical incision and collection. In some cases, a biosensor may comprise a unit/element configured to collect samples. Alternatively the sample may be collected by a separate equipment.

2. Analyte preparation: Once the colon tissue is obtained, the genomic DNA of the tissue can be obtained also by a variety of methods present in the art such as an alkaline lysis extraction method of DNA. In some cases, a biosensor may comprise a unit/element configured to prepare analytes, whereas in some other cases, the preparation of analytes may be done separately and the prepared analytes may be provided to a biosensor.

In one example (Example 5A), the genomic DNA may be obtained and further fragmented to be suitable to hybridize with the probes via physical methods and/or chemical methods. Physical methods of DNA fragmentation may include, but not limited to, sonication of DNA. Chemical methods of DNA fragmentation may include, but not limited to, restriction with nucleases. In some embodiment, the physical and chemical methods can be applied to the genomic DNA together.

In another example (Example 5B), using specific primers to the target region of the APC gene, amplification of the target nucleotide sequence can be performed. In some cases, the primers used in this amplification may comprise a 5' anchor region, a 3' extension region and a bubble region as described in elsewhere in the specification. Once the analyte comprising the target region of the APC gene and primer sequences is obtained from the amplification reaction (e.g. PCR), it can be treated with a certain nucleases to remove at least part of the primer sequences. Such embodiments would be desirable if one or more nuclease recognition sequence(s) are present in the 5' anchor region and/or the bubble region of the primers. In some other cases, however, the primers may not comprise one or more of the 5' anchor region, a 3' extension region and a bubble region and may not be cleaved with nucleases. In such cases, the amplified analytes may proceed to the hybridization with the probes without nuclease treatment.

3. Probe preparation: According to the methods as disclosed in Example 1, the probes specific to the target region of the human APC gene can be prepared in this particular example. The primers used for this probe preparation may comprise a 5' anchor region; a 3' extension region and a bubble region and one or more of nuclease cleavage sites may present in the 5' anchor region and/or the bubble region. Once the target sequences are amplified with the specific primers, at least part of the primer sequences can be removed by nuclease treatment. As such, the resulting target sequences, which will be used as probes, can be substantially consistent in size. The prepared probes can be linked to nanostructures/nanosensors (e.g. nanowires, nanotubes, nanobeads, nanopores, nanogaps and others) by a variety of methods available in the art. If more than one types of colon cancer wish to be tested, multiple kinds of probes (i.e. probes specific to different target regions of the APC gene) may be prepared and linked to the nanosensors. In some cases, a biosensor may comprise a unit/element configured to prepare probes, whereas in some other cases, the preparation of probes may be done separately and the prepared probes may be provided to a biosensor.

4. Hybridization of the target sequence with the probe and removal of flanking sequences from the target sequence: In some examples, especially when the analyte is prepared according to the Example 5A, the analyte may comprise addition sequences that are not part of the target sequences. In such examples, once the probe and the analyte are hybridized, the additional sequences present in the analyte that are not part of the target sequences may be present as single stranded DNAs. These single stranded flanking sequences can be removed by treatment of one or more of nucleases. In some cases, S1 nuclease, that may remove the single stranded DNA, can be treated to remove the flanking single stranded DNA sequences. Once the flanking sequences are removed, the detection of the signals by the nanostructures may continue. In some examples, one or more washing steps may be further added to remove the degraded flanking nucleotides from the reaction mixture. Moreover, the melting or dissociation of the duplex after removing the flanking nucleotide sequences may occur and re-hybridization of the processed analytes and the probes may be operated. Alternatively, after the removal of the flanking sequence, the detection of the signals by the nanostructures/nanosensors may be operated without such melting and re-hybridization steps. As disclosed in elsewhere in the specification, the recruitment of the target sequence to the probe can cause changes in the charge at, or near their surfaces, or across the nanostructures. Stringency of hybridization between the probe and the target sequences (having sequence variations in some cases) can be further controlled by manipulating various factors such as pH, salt concentration, and/or temperature of the reaction environment. Once the signals are sensed individually or collectively from a plurality of the nanostructures, these signal data can be further processed if desired. In some cases, a biosensor may comprise a unit/element configured to perform the hybridization with the probe. In certain some examples, this hybridization unit with the probe is operably coupled to other unit/elements such as a sample collection unit, asample preparation unit and/or aprobe preparation unit.

5. Data processing: Depending on the experimental settings, a variety of kinds of data, indicating, for example, the presence of certain mutation allele(s) of the APC gene in the test individual, the abundance of the certain mutation allele(s) of APC in the individual and the determination of specific mutation(s) of APC in the tested individual, can be obtained. In some cases, a biosensor may comprise a unit/element configured to process data obtained from the nanostructures. In certain some examples, this data processing unit is operably coupled to other unit/element(s) of a biosensor, or alternatively can be separately oeprated.

6. Generation of report: Once the detection data are processed and desired results are obtained (e.g. presence and/or abundance of concerned APC mutations and its corresponding cancer type), such information may be generated in a form of report to provide a medical practitioner and/or the tested individual. In some cases, the biosensor may comprise a unit/element configured to generate a report obtained from the nanostructures/nanosensors. In certain some examples, this report generation unit is operably coupled to other unit/element(s) of a biosensor, or alternatively can be separately oeprated.

Example 7

Detection of Analytes with a Biosensor-III

Example 7 presents still another embodiment of the present invention using an illustrative scenario of human APC gene detection.

1. Sample collection: To determine somatic mutation of APC gene in an individual, some colon tissues can be obtained by a variety of methods available in the art such as a surgical incision and collection. In some cases, a biosensor may comprise a unit/element configured to collect samples. Alternatively the sample may be collected by a separate equipment.

2. Analyte preparation: Once the colon tissue is obtained, the genomic DNA of the tissue can be obtained also by a variety of methods present in the art such as an alkaline lysis extraction method of DNA. In some cases, a biosensor may comprise a unit/element configured to prepare analytes, whereas in some other cases, the preparation of analytes may be done separately and the prepared analytes may be provided to a biosensor.

In one example (Example 5A), the genomic DNA may be obtained and further fragmented to be suitable to hybridize with the probes via physical methods and/or chemical methods. Physical methods of DNA fragmentation may include, but not limited to, sonication of DNA. Chemical methods of DNA fragmentation may include, but not limited to, restriction with nucleases. In some embodiment, the physical and chemical methods can be applied to the genomic DNA together.

In another example (Example 5B), using specific primers to the target region of the APC gene, amplification of the target nucleotide sequence can be performed. In some cases, the primers used in this amplification may comprise a 5' anchor region, a 3' extension region and a bubble region as described in elsewhere in the specification. Once the analyte comprising the target region of the APC gene and primer sequences is obtained from the amplification reaction (e.g. PCR), it can be treated with a certain nucleases to remove at least part of the primer sequences. Such embodiments would be desirable if one or more nuclease recognition sequence(s) are present in the 5' anchor region and/or the bubble region of the primers. In some other cases, however, the primers may not comprise one or more of the 5' anchor region, a 3' extension region and a bubble region and may not be cleaved with nucleases. In such cases, the amplified analytes may proceed to the hybridization with the probes without nuclease treatment.

3. Probe preparation: According to the methods as disclosed in Example 1, the probes specific to the target region of the human APC gene can be prepared in this particular example. The primers used for this probe preparation may comprise a 5' anchor region, a 3' extension region and a bubble region and one or more of nuclease cleavage sites may present in the 5' anchor region and/or the bubble region. Once the target sequences are amplified with the specific primers, at least part of the primer sequences can be removed by nuclease treatment. As such, the resulting target sequences, which will be used as probes, can be substantially consistent in size. The prepared probes can be linked to nanostructures/nanosensors (e.g. nanowires, nanotubes, nanobeads, nanopores, nanogaps and others) by a variety of methods available in the art. If more than one types of colon cancer wish to be tested, multiple kinds of probes (i.e. probes specific to different target regions of the APC gene) may be prepared and linked to the nanosensors. In some cases, a biosensor may comprise a unit/element configured to prepare probes, whereas in some other cases, the preparation of probes may be done separately and the prepared probes may be provided to a biosensor.

4. Hybridization of the analyte and the oligonucleotides: In some examples, especially when the analyte is prepared according to the Example 5A, the analyte may comprise additional flanking sequences that are not part of the target sequences. In such examples, the analyte can be hybridized with some oligonucleotides, which are substantially complementary to the target sequences. Once the oligonucleotides and the analyte are hybridized, the additional sequences present in the analyte that are not part of the target sequences may be present as single stranded DNAs. These single stranded flanking sequences can be removed by treatment of one or more of nucleases. In some cases, S1 nuclease, that may remove the single stranded DNAs, can be treated to remove the flanking single stranded DNA sequences. Once the flanking sequences are removed, the duplex of the target sequence and the oligonucleotides may be dissociated or melted and the target sequence can be specifically collected. In some cases, a biosensor may comprise a unit/element configured to perform the hybridization with the oligonucleotide. In certain some examples, this hybridization with the oligonucleotide is operably coupled to other unit/elements such as a sample collection unit, a sample preparation unit and/or a probe preparation unit.

5. Hybridization of the target sequence with the probe: The target sequence after removal of the flanking sequences can be provided to the array of nanostructures comprising the probes. Such hybridization may occur in a liquid condition or gas condition. As disclosed in elsewhere in the specification, the recruitment of the target sequence to the probe can cause changes in the charge at, or near their surfaces, or across the nanostructures. Stringency of hybridization between the probes and the target sequences (having sequence variations in some cases) can be controlled by manipulating various factors such as pH, salt concentration, and/or temperature of the reaction environment. Once the signals are sensed individually or collectively from the plurality of nanostructures, these signal data can be further processed if desired. In some cases, a biosensor may comprise a unit/element configured to perform the hybridization. In certain some examples, this hybridization unit is operably coupled to other unit/elements such as a sample collection unit, a sample preparation unit and/or a probe preparation unit.

6. Data processing: Depending on the experimental settings, a variety of kinds of data, indicating, for example, the presence of certain mutation allele(s) of the APC gene in the test individual, the abundance of the certain mutation allele(s) of APC in the individual and the determination of specific mutation(s) of APC in the tested individual, can be obtained. In some cases, a biosensor may comprise a unit/element configured to process data obtained from the nanostructures. In certain some examples, this data processing unit is operably coupled to other unit/element(s) of a biosensor, or alternatively can be separately operated.

7. Generation of report: Once the detection data are processed and desired results are obtained (e.g. presence and/or abundance of concerned APC mutations and its corresponding cancer type), such information may be generated in a form of report to provide a medical practitioner and/or the tested individual. In some cases, the biosensor may comprise a unit/element configured to generate a report obtained from the nanostructures/nanosensors. In certain some examples, this report generation unit is operably coupled to other unit/element(s) of a biosensor, or alternatively can be separately operated.

What is claimed is:

1. A method of detecting at least one target nucleotide sequence, the method comprising:
    amplifying the at least one target nucleotide sequence with one or more primers comprising a 5' anchor region, a 3' extension region, and a bubble region therebetween, wherein the bubble region comprises a nuclease recognition sequence for a restriction enzyme and a cleavage site for said restriction enzyme;

treating the amplified nucleotide sequence with said restriction enzyme so as to remove the 5' anchor region and part of the bubble region from the amplified nucleotide sequence, thereby generating a probe, wherein said probe comprises the 3' extension region and a remaining part of the bubble region;

contacting the at least one target nucleotide sequence with the probe under hybridizing conditions; and detecting a signal related to the presence, level, and/or sequence variation of the target nucleotide sequence;

wherein the 5' anchor region is about 15 to 30 bp, is configured to hybridize to a nucleotide sequence outside of the target nucleotide sequence, and is about 70 to 100% complementary to said nucleotide sequence outside of the target nucleotide sequence;

the 3' extension region is about 5 to 30 bp and about 80 to 100% complementary to a portion of the target nucleotide sequence; and the bubble region is about 50% or less complementary to the target nucleotide sequence.

2. The method of claim 1, wherein the at least one target nucleotide sequence is selected from the group consisting of DNA, RNA, and any derivatives thereof.

3. The method of claim 1, wherein the one or more primers further comprise a nucleotide sequence that can be cleaved by a restriction enzyme in the 5' anchor region.

4. The method of claim 1, wherein said nucleotide sequence in the bubble region that can be cleaved by said restriction enzyme is not present in either the 3' extension region or the target nucleotide sequence.

5. The method of claim 1, wherein the probe is selected from the group consisting of DNA, RNA, and any derivatives thereof.

6. The method of claim 1, wherein the probe is immobilized on a conducting medium.

7. The method of claim 6, wherein said conducting medium is selected from the group consisting of a nanowire, a nanotube, a nanogap, a nanopore, a nanobead, and any other nanostructure capable of conducting an electrical current.

8. The method of claim 7, wherein the signal is generated when hybridization of the at least one target nucleotide sequence to the probe causes a change in the electrical charge of the probe.

9. The method of claim 1, wherein sequence variations in the target nucleotide sequence are detected.

10. The method of claim 1, wherein two or more of the presence, level and sequence variation of the target nucleotide sequence are detected simultaneously.

11. The method of claim 1, further comprising generating two or more types of probes, each of which comprises a different nucleotide sequence.

12. A method of detecting at least one target nucleotide sequence, the method comprising:

obtaining the at least one target nucleotide sequence;

contacting the at least one target nucleotide sequence with a probe, which is immobilized on a conducting medium, under hybridizing conditions, wherein the probe is at least partially complementary to the target nucleotide sequence, such that the probe hybridizes to the target nucleotide sequence, thereby generating a duplex of the target nucleotide sequence and the probe;

removing single-stranded nucleotide sequences that are not present in the duplex; and detecting a signal related to the presence, level and/or sequence variation of the target nucleotide sequence;

wherein the probe is generated by:

amplifying the at least one target nucleotide sequence with one or more primers comprising a 5' anchor region, a 3' extension region, and a bubble region therebetween, wherein said bubble region comprises a nuclease recognition sequence for a restriction enzyme and a cleavage site for said restriction enzyme; and treating the amplified nucleotide sequence with said restriction enzyme so as to remove the 5' anchor region and part of the bubble region from the amplified nucleotide sequence, thereby generating a probe, wherein said probe comprises the 3' extension region and a remaining part of the bubble region; and wherein the 5' anchor region is about 15 to 30 bp, is configured to hybridize to a nucleotide sequence outside of the target nucleotide sequence, and is about 70 to 100% complementary to said nucleotide sequence outside of the target nucleotide sequence;

the 3' extension region is about 5 to 30 bp and about 80-100% complementary to a portion of the target nucleotide sequence; and the bubble region is about 50% or less complementary to the target nucleotide sequence.

13. The method of claim 12, wherein the 5' anchor region further comprises a nuclease cleavage sequence.

14. The method of claim 12, wherein the at least one target nucleotide sequence is obtained by one of the following methods:

amplifying the at least one target nucleotide sequence with one or more primers comprising nucleotide sequences corresponding to part of the at least one target nucleotide sequence, obtaining nucleotide sequences from an organism and shearing the nucleotide sequences into a size suitable for contacting with the probe, or obtaining nucleotide sequences from an organism and shearing the nucleotide sequences using one or more nucleases into a size suitable for contacting with the probe.

15. The method of claim 12, wherein removing single-stranded nucleotide sequences comprises cleaving single-stranded nucleotide sequences using one or more nucleases.

16. The method of claim 15, wherein said one or more nucleases are selected from the group consisting of sequence-specific nucleases.

17. The method of claim 15, wherein said one or more nucleases are selected from the group consisting of S1 nuclease, P1 nuclease, micrococcal nuclease, mung bean nuclease, exonuclease II, III, IV, V, VI, VII and VIII, and Klenow fragment.

18. The method of claim 15, wherein said one or more nucleases are selected from the group consisting of sequence-nonspecific nucleases.

19. The method of claim 12, wherein said conducting medium is selected from the group consisting of a nanowire, nanotube, nanogap, nanopore, nanobead, and any other nanostructure that is able to conduct electricity.

20. The method of claim 19, wherein the signal is generated when hybridization of the target nucleotide sequence to the probe causes a change in the electrical charge of the probe.

* * * * *